United States Patent [19]

Sullivan, 3rd et al.

[11] 4,039,336
[45] Aug. 2, 1977

[54] DIACETYLENIC ALCOHOL CORROSION INHIBITORS

[75] Inventors: Daniel S. Sullivan, 3rd, Houston, Tex.; Charles E. Strubelt, Tamare, Venezuela; Kenneth W. Becker, Houston, Tex.

[73] Assignee: Exxon Research and Engineering Company, Linden, N.J.

[21] Appl. No.: 637,302

[22] Filed: Dec. 3, 1975

[51] Int. Cl.$^2$ .............................................. C09D 5/08
[52] U.S. Cl. ................................ 106/14; 252/8.55 E; 252/181; 252/396
[58] Field of Search ................ 252/87, 181, 388, 396, 252/8.55 E, 146; 260/617 E; 106/14

[56] References Cited

U.S. PATENT DOCUMENTS

| | | | |
|---|---|---|---|
| 2,913,408 | 11/1959 | Pumpelly et al. | 260/617 E |
| 3,404,094 | 10/1968 | Keeney | 252/396 |
| 3,428,566 | 2/1969 | Herman et al. | 252/388 |
| 3,755,469 | 8/1973 | Pasedach et al. | 260/617 E |

Primary Examiner—Lorenzo B. Hayes
Attorney, Agent, or Firm—D. A. Roth; C. L. Kim

[57] ABSTRACT

The corrosion of ferrous metals by corrosive acids at elevated temperatures is inhibited by adding to environments containing the acids an effective amount of a novel α, Ω (hereinafter "alpha", "omega", respectively) diacetylenic diol (e.g., with two acetylenic functionalities) having the structural formula:

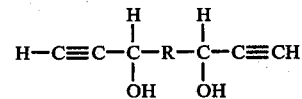

where R is an aliphatic, alicyclic or aromatic residue containing from 1 to about 12 carbon atoms and may include one or more functional groups such as halogen atoms, carbonyl, carboxyl, carbamyl, amino, formyl or nitroso radicals or other functional groups without impaired performance. The diacetylenic diols may be employed in combination with other corrosion inhibitors.

6 Claims, No Drawings

DIACETYLENIC ALCOHOL CORROSION INHIBITORS

BACKGROUND OF THE INVENTION

1. Field of the Invention

This invention relates to corrosion inhibitor compositions useful for retarding the corrosion of ferrous metals by corrosive acids especially for metals in an underground oil field location, and is particularly concerned with novel diacetylenic alcohols which are especially effective corrosion inhibitors.

2. Description of the Prior Art

The use of acetylenic alcohols for inhibiting the corrosion of ferrous metals has been proposed in the past. Although compounds such as propargyl alcohol which contain one acetylenic linkage and one hydroxyl group have been found effective, studies have shown that certain acetylenic diols perform very poorly. These materials have the following structures:

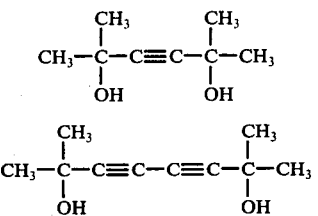

It has been postulated that one reason for this may be that the diols undergo an acid catalyzed cyclization to form a dihydrofuran as indicated by Formula III below or undergo water elimination to produce the conjugated ENE-YNE structure indicated by formula IV below.

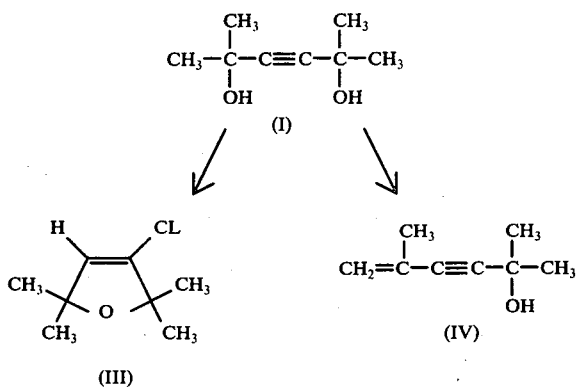

It may also be that ethynyl hydrogen group, — C ≡ C — H, and a carbinol group attached directly to the acetylenic linkage,

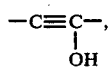

are important if the acetylenic compound is to be an effective acid corrosion inhibitor. Any compound employed for this purpose should not be sterically hindered.

SUMMARY OF THE INVENTION

The present invention provides a novel class of acetylenic diol compositions which are surprisingly effective as corrosion inhibitors for ferrous metals. The improved inhibitors of the invention have the general formula:

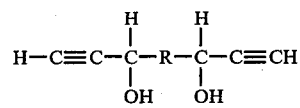

where R is an aliphatic, alicyclic or aromatic residue containing from 1 to about 12 carbon atoms and may include one or more functional groups such as halogen atoms, carbonyl, carboxyl, carbamyl, amino, formyl or nitroso radicals or other functional groups without impaired performance.

The preferred diacetylenic diols of the invention are those prepared from alkyl residues and have the following structural formula:

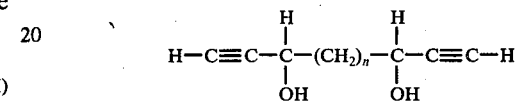

where $n$ is an integer from 1 to 12, preferably from 4 to 8. Examples of such compounds include 3,5-dihydroxy-1,6-heptadiyne, 3,6-dihydroxy-1,7-octadiyne, 3,7-dihydroxy-1,8-nonadiyne, 3,8-dihydroxy-1,9-decadiyne, 3,10-dihydroxy-1,11-dodecadiyne, 3,12-dihydroxy-1,13-tetradecadiyne, 3,14-dihydroxy-1,15-hexadecadiyne, and the like. Such compounds have excellent corrosion inhibiting properties and do not readily undergo dehydrocyclization and other reactions which destroy their effectiveness.

These diacetylenic diols are used to inhibit the corrosion of ferrous metals such as steel by hydrochloric acid, sulfuric acid, nitric acid and other corrosive acid solutions by adding them to the solutions containing these acids in effective concentrations. The materials of the invention are particularly effective for combatting corrosion at elevated temperatures and below ground in an oil field environment.

DESCRIPTION OF THE PREFERRED EMBODIMENTS

The alpha, omega diacetylenic diol compositions of the invention may be prepared in a number of different ways. Suitable starting materials include, the alpha, omega dialdehydes such as succinic dialdehyde, malonic dialdehyde, adipaldehyde, sebacic aldehyde and the like. They also may be made from alpha, omega dialdehyde precursors such as alpha, omega dinitriles, cyclic olefins such as cyclohexene and cycloheptene, and 1,2 cyclohexane diol.

The dialdehydes can be prepared by the partial reduction of the dinitriles, by the reductive ozonization of cyclic olefins as described by F. G. Fisher and K. Lowcubert, Chem. Ber. 66, 666 (1933), or by oxidation of 1,2 cyclohexane diol or similar dihydroxy alicyclic compounds in the presence of lead acetate as described by Stanley R. Sandler and Wolf Karo, "Organic Functional Group Preparations," page 149, Academic Press, New York, N.Y. (1968), and by J. English and E. W. Barber, General American Chemical Society, 71 3310 (1949). Certain of the dialdehydes are used as chemical intermediates in the manufacture of nylon and related products and are available from commercial sources. The use of adipaldehyde and similar dialdehydes containing a total of from about 6 to about 14 carbon atoms per molecule as starting materials is generally preferred.

The dialdehydes which are employed as the preferred starting materials for the preparation of the diacetylenic alcohols can be converted into the corresponding alcohols by a variety of different methods. Several such methods are described by Thomas F. Rutledge in "Acetylenic Compounds," Reinhold Book Corporation, New York, New York (1968). One such method involves treatment of the dialdehyde with ethynyl magnesium bromide in tetrahydrofuran as described by Lars Skatterbol, E. R. H. Jones and Mark C. Whiting in Org. Syn. Coll., Vol. IV, pp. 792–795 (1963). Other methods which may be used for production of the diacetylenic alcohols will be familiar to those skilled in the art.

The diacetylenic alcohols which are prepared as described above have the general formula

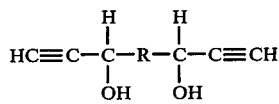

where R is an aliphatic, alicyclic or aromatic residue containing from 1 to about 12 carbon atoms and may include one or more other functional groups such as halogen atoms, carbonyl, carboxyl, carbamyl, amino, formyl or nitroso radicals or other functional groups without impaired performance.

The alpha, omega diacetylenic alcohols which have been prepared from alkyl residues are preferred for purposes of the invention. These diols have the following structural formula:

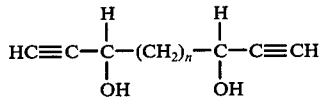

wherein $n$ is a small number from 1 to 12, preferably from about 4 to 8. Compounds of this type which are corrosion inhibitors in accordance with the invention include 3,5-dihydroxy-1,6-hepadiyne, 2,6-dihydroxy-1,7-octadiyne, 3,7-dihydroxy-1,8-nonadiyne, 3,8-dihydroxy-1,9-decadiyne, 3,7-dihydroxy-5-methyl-1,8-nonadiyne, 3,8-dihydroxy-6-dimethyl-1,9-decadiyne, 3,10-dihydroxy-5-methyl-7-ethyl-1,11-dodecadiyne, 3,12-dihydroxy-7,8-dimethyl-1,13-tetradecadiyne, 3,12-dihydroxy-1,13-tetradecadiyne, 3,14-dihydroxy-7,8,9-trimethyl-1,15-hexadecadiyne, 3,14-dihydroxy-1,15-hexadecadiyne and the like.

The alpha, omega diacetylenic alcohols are useful for inhibiting the corrosion of iron, steel, stainless steel and other ferrous metals by nonoxidizing acids such as hydrochloric acid, sulfuric acid, phosphoric acid, acetic acid and the like. They are useful at atmospheric temperatures as well as at elevated temperatures up to about 200° F and in some cases even higher. They are effective with both dilute and concentrated acids, including commerical concentrated hydrochloric acid of 37% strength. Applications in which they are particularly useful include oil well acidizing, metal pickling, cleaning and polishing baths, boiler cleaning compositions and the like.

The novel diols of the invention are generally utilized by dissolving or dispersing them, alone or in combination with other materials, in the acid solution which is to be inhibited. Other standard inhibitor constituents can be employed in conjunction with the diols such as surface active agents, wetting compounds, long chain aliphatic amines, alkaryl, polyethylene oxyethanol, quaternary derivatives of heterocyclic nitrogen compounds and halomethylated aromatic compounds, perfluoroalkylimidazolines and the like. The diols are normally employed in concentrations between about 0.005% and about 2.0%, preferably 0.05% to 1.0%, based on the volume of the aqueous acid solutions to which they are added, and are particularly effective when used in concentrations between about 0.1 and about 1.0% by volume.

The nature and objects of the invention are further illustrated by the following examples.

EXAMPLE 1

Adipaldehyde was prepared by the oxidation of cyclohexane diol with lead acetate using the procedure described by Sandler and Karo in "Organic Functional Group Preparation," page 149, Academic Press, New York, New York (1968). The adipaldehyde was then converted to 3,8-dihydroxy-1,9-decadiyne by treatment with ethynyl magnesium bromide in tetrahydrofuran by first fitting a 1000 ml of three-neck flask with a stirrer, addition funnel, nitrogen tube and condenser.

Into this were placed 24 g. of magnesium turnings and 300 ml of anhydrous tetrahydrofuran. A solution of 100 g. of ethylbromide in anhydrous tetrahydrofuran was then slowly added to the magnesium turnings until the formation of ethyl magnesium bromide was complete. This step and the subsequent reaction steps were carried out under dry nitrogen gas.

The ethyl magnesium-bromide solution was then transferred to a large pressure equalizing addition funnel by means of a bent glass tube and nitrogen pressure. 400 ml of tetrahydrofuran was then placed in a dry glass 200 ml reaction kettle equipped with a gas inlet tube, a thermometer, a stirrer, and the pressure equalizing addition funnel. Acetylene was added to the gas dispersion tube with slow addition of the ethyl magnesium bromide. This was continued until the formation of ethynyl magnesium bromide was complete.

The ethynyl magnesium bromide prepared as described above was cooled in an ice-methanol bath. A solution of 39.0 g. of adipaldehyde in 50 ml of anhydrous tetrahydrofuran was added to the stirred ethynyl magnesium bromide solution. After addition had been completed, the mixture was allowed to warm to room temperature with stirring over a period of 10 hours.

The reaction mixture was then added to a 4-liter separatory funnel containing 1.5 liters of saturated aqueous ammonium chloride solution. The resulting mixture was shaken and then allowed to separate into an organic top phase and aqueous lower phase. The organic phase was removed and the lower phase was then extracted three times with ether to recover any organic materials present.

Following this, the organic phase and ether solutions were combined, dried over magnesium sulfate, and filtered. The ether and tetrahydrofuran were removed from the filtrate by distillation. Vacuum distillation of the product, which had a boiling point between 130° and 141° C at 9 mm of mercury, yielded a clear viscous liquid that slowly solidified after several days. The yield was 39.2 g., 69% of the theoretical yield of 3,8-dihydroxy-1,9-decadiyne. Analysis showed an empirical formula of $C_{10}H_{14}O_2$. Infrared spectrum analysis and proton magnetic resonance spectrum analysis confirmed that the product obtained was 3,8-dihydroxy-1,9-decadiyne.

EXAMPLE 2

Corrosion tests were carried out using propargyl alcohol and 3,8-dihydroxy-1,9-decadiyne prepared as described in Example 1 above. These tests were conducted by preparing 100 ml samples of 15% hydrochloric acid in separate sample bottles. Test coupons of steel cut from J-55 oil well tubing were placed in the sample bottles and 0.5% by volume of the selected inhibitors were added to the bottles. The bottles were then held at a temperature of 200° F and at ambient pressure for a period of 4 hours. Following this, the samples were moved from the acid solution, washed repeatedly to remove any remaining acid, and then dried. The dried samples were weighed to determine the weight loss and permit calculation of the corrosion rate. The results obtained are shown in Table I below:

TABLE I

| Corrosion Tests | | |
|---|---|---|
| Inhibitor | Weight Loss, grams | Corrosion Rate lb/ft² |
| $HC \equiv C - \underset{\underset{H}{\mid}}{\overset{\overset{H}{\mid}}{C}} - OH$ | 0.3050 | 0.0216 |
| $HC \equiv C - \underset{\underset{OH}{\mid}}{\overset{\overset{H}{\mid}}{C}} - (CH_2)_4 - \underset{\underset{OH}{\mid}}{\overset{\overset{H}{\mid}}{C}} - C \equiv CH$ | 0.0412 | 0.00292 |

It is noted from the above table that the corrosion rate with the 3,8-dihydroxy-1,9-decadiyne was nearly an order of magnitude lower than that with the propargyl alcohol. This low corrosion rate under the relatively severe conditions of the test demonstrates that the alpha, omega diacetylenic alcohols are surprisingly more effective as corrosion inhibitors than propargyl alcohol and similar materials employed in the past.

EXAMPLE 3

Following the work reported above, additional corrosion tests were carried out with three different grades of steel used in oil well tubing and three acetylenic alcohols. One of the alcohols was 3,8-dihydroxy-1,9-decadiyne prepared as described in Example 1 above and the other two were acetylenic alcohols outside the scope of this invention. One of these was 2,5-dimethyl-3-yn3-2,5-diol and the other was 2,7-dimethyl-3,5-octadiyne-2,7 diol. Sample bottles containing 100 ml of 15% hydrochloric acid and weighed steel corrosion coupons were prepared as described in Example 2.

To each of these bottles were added one of the acetylenic alcohols in a concentration of 0.25 or 0.5% by volume. The bottles were then held at 200° F and ambient pressure for a period of 4 hours. Following this, the samples were removed, washed and dried, and weighed to permit determination of the weight loss and corrosion rate. Results are shown in Table II.

TABLE II

| Comparative Corrosion Tests | | | | |
|---|---|---|---|---|
| Inhibitor | Inhibitor Concentration, Vol. % | Steel Coupon | Weight Loss, g. | Corrosion Rate, lb/ft² |
| 3,8-Dihydroxy-1,9-decadiyne | 0.25 | P 105 | 0.5916 | 0.0420 |
| " | 0.25 | N 80 | 0.6110 | 0.0434 |
| " | 0.25 | J 55 | 0.1437 | 0.0102 |
| " | 0.50 | P 105 | 0.0809 | 0.00574 |
| " | 0.50 | N 80 | 0.0432 | 0.00307 |
| " | 0.50 | J 55 | 0.0350 | 0.00248 |
| 2,5-Dimethyl-3-yne-2,5-diol | 0.25 | P 105 | 12.2687 | 0.942 |
| " | 0.25 | N 80 | 13.3726 | 0.950 |
| " | 0.25 | J 55 | 10.2762 | 0.730 |
| " | 0.50 | P 105 | 13.3492 | 0.948 |
| " | 0.50 | N 80 | 13.3404 | 0.947 |
| " | 0.50 | J 55 | 11.8972 | 0.845 |
| 2,7-Dimethyl-3,5-octadiyne-2,7-diol | 0.25 | P 105 | 13.1646 | 0.935 |
| " | 0.25 | N 80 | 11.8172 | 0.839 |
| " | 0.25 | J 55 | 12.3035 | 0.874 |
| " | 0.50 | P 105 | 12.9889 | 0.922 |
| " | 0.50 | J 55 | 10.8834 | 0.708 |

Again, it can be seen that the alpha, omega diacetylenic alcohols of the invention are surprisingly more effective than closely related acetylenic alcohols which lack the structure of the materials of the invention.

What is claimed is:

1. A relatively non-corrosion composition of matter comprising water and a quantity of nonoxidizing acid sufficient to form an aqueous acid ordinarily corrosive to ferrous metals, wherein the corrosive tendency of said aqueous acid to ferrous metals is substantially diminished by the presence of about 0.005 to 2.0 vol. % of an α, Ω-diacetylenic diol having the structural formula:

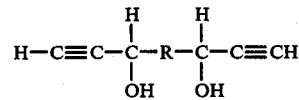

where R is an aliphatic, alicyclic or aromatic residue containing from 1 to 12 carbon atoms.

2. The composition according to claim 1 wherein said diacetylenic diol is 3,8-dihydroxy-1,9-decadiyne.

3. The composition of claim 1 wherein said diacetylenic diol has the structural formula:

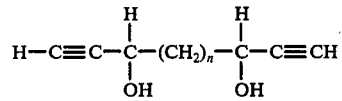

wherein n is an integer ranging from 1 to 12.

4. The composition of claim 3 wherein said n is an integer ranging from 4 to 8.

5. A process for inhibiting the corrosion of ferrous metals in contact with aqueous nonoxidizing acid, said process consisting essentially of maintaining in said acid an effective amount of between about 0.005 to about 2.0 vol. % of an α, Ω-diacetylenic diol having the structural formula:
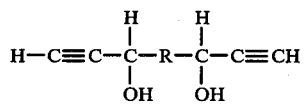
where R is an aliphatic, alicyclic or aromatic residue containing from 1 to 12 carbon atoms.
6. A process according to claim 5 wherein said diol is 3,8-dihydroxy-1,9-decadiyne.
* * * * *